April 30, 1946. A. F. WATKINS Plant Pat. 687
ROSE PLANT
Filed June 30, 1945
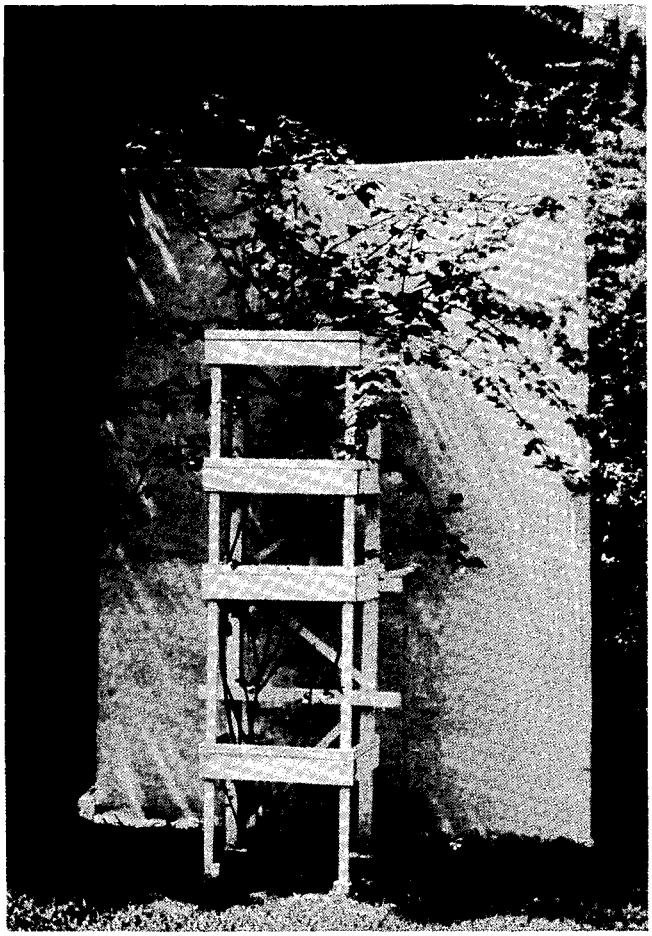
Inventor
A. F. Watkins
By Robb & Robb
His Attorneys Patented Apr. 30, 1946

Plant Pat. 687

UNITED STATES PATENT OFFICE

687

ROSE PLANT

Archibald F. Watkins, Tyler, Tex., assignor to Krider Nurseries, Inc., Middlebury, Ind., a corporation of Indiana Application June 30, 1945, Serial No. 602,481

1 Claim. (Cl. 47—61)

The present discovery relates to a new and distinct variety of rose plant, originating as a sport of the rose "Festival" (Pl. Pat. No. 545), and distinguishing therefrom dominantly by its climbing habit.

The parent plant, itself a sport of "E. G. Hill," is a bush rose of the hybrid tea class, and is notable for its thornlessness and the smooth edges of its foliage. Its bloom, in general tonality, is of the attractive color Rose Red (Ridgway, Plate XII) in the newly opened flower, changing to Tyrian Rose (Ridgway, Plate XII) as the flower develops.

Of primary importance here, however, is the fact that this parent variety has never, so far as I am aware, exhibited a climbing habit, the height of growth being on the average, approximately of the order of 2½′ to 3′.

The present variety was discovered by me in a nursery field devoted entirely to this bush, "Festival" variety, above referred to, exhibiting the unusual vigorous growth to a height of ten to eleven feet and more when grown under comparable conditions.

The accompanying illustration shows a specimen of this variety in association with a background screen, the height of the latter being 9′ 6″. The plant thus shows a height in excess of ten feet.

Aside from this climbing habit, the new variety has the same general characteristics that are present in its bush, thornless parent, including the primary feature of thornlessness, the smooth edges of the leaves, the color of the flowers, etc. It is, therefore, unnecessary to describe the plant in detail since it conforms to the description contained in the above-mentioned patent for the parent variety, excepting only as to the parent's habit of growth as a bush.

The new variety has been asexually reproduced by budding, and the climbing characteristic noted appeared to be fully established in the progeny.

I claim:

A new and distinct variety of rose plant, characterized as to novelty by its vigorous climbing habit, in combination with foliage having smooth to very slightly serrated edges, and total absence of thorns or prickles on any part of the plant, substantially as described.

ARCHIBALD F. WATKINS.